(12) United States Patent
Iwatschenko et al.

(10) Patent No.: US 10,737,088 B2
(45) Date of Patent: Aug. 11, 2020

(54) DEVICE FOR PROVIDING A CONSTANT AMOUNT OF AEROSOL

(71) Applicant: Fraunhofer-Gesellschaft zur Förderung der angewandten Forschung e.V., München (DE)

(72) Inventors: Peter Iwatschenko, Eckenthal (DE); Gerhard Pohlmann, Meerbeck (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 808 days.

(21) Appl. No.: 15/123,557

(22) PCT Filed: Mar. 2, 2015

(86) PCT No.: PCT/EP2015/054244
§ 371 (c)(1),
(2) Date: Sep. 2, 2016

(87) PCT Pub. No.: WO2015/132174
PCT Pub. Date: Sep. 11, 2015

(65) Prior Publication Data
US 2017/0065811 A1   Mar. 9, 2017

(30) Foreign Application Priority Data

Mar. 5, 2014   (EP) .................................. 14157865

(51) Int. Cl.
*A61M 39/24* (2006.01)
*A61M 11/06* (2006.01)
(Continued)

(52) U.S. Cl.
CPC ............ *A61M 39/24* (2013.01); *A61M 11/06* (2013.01); *A61M 15/0013* (2014.02);
(Continued)

(58) Field of Classification Search
CPC .............. A61M 11/06; A61M 15/0013; A61M 15/0065; A61M 16/0003; A61M 16/0057;
(Continued)

(56) References Cited

U.S. PATENT DOCUMENTS 3,861,195 A * 1/1975 vom Hagen ............. G01N 7/14
137/487.5
3,896,849 A * 7/1975 Ervin .................... F16K 15/147
137/847
(Continued)

FOREIGN PATENT DOCUMENTS

CN   101189071 A   5/2008
CN   102271746 A   12/2011
(Continued)

OTHER PUBLICATIONS

Office Action, Japanese Patent Application No. 2016-555553, dated Dec. 4, 2018 with English translation (8 pages).
(Continued)

*Primary Examiner* — Kendra D Carter
*Assistant Examiner* — Brian M. Booker
(74) *Attorney, Agent, or Firm* — Hamre, Schumann, Mueller & Larson, P.C.

(57) ABSTRACT

The invention relates to a device (10) for providing an aerosol from an aerosolizable material, the device comprising an aerosolization unit (300) through which pressure pulses of a carrier gas (60) are passed; a reservoir (100) comprising the aerosolizable material and which provides the aerosolizable material to the aerosolization unit (300) where the aerosolizable material is entrained by the carrier gas (60); a material providing valve (210) located between the reservoir (100) and the aerosolization unit (300) which opens in direction of the aerosolization unit (300) and which is opened and closed by a pressure difference between the
(Continued)

reservoir (100) and the aerosolization unit (300) and which provides, in an open state, the aerosolizable material to the aerosolization unit (300).

16 Claims, 8 Drawing Sheets

(51) Int. Cl.
*A61M 15/00* (2006.01)
*A61M 16/16* (2006.01)
*B05B 7/14* (2006.01)
*F16K 15/14* (2006.01)
*A61M 16/20* (2006.01)
*A61M 16/00* (2006.01)
*F16K 15/18* (2006.01)
*G01N 21/53* (2006.01)
*A61M 16/08* (2006.01)
*A61M 16/14* (2006.01)
*A61M 16/10* (2006.01)
*B05B 1/32* (2006.01)

(52) U.S. Cl.
CPC .... *A61M 15/0065* (2013.01); *A61M 16/0003* (2014.02); *A61M 16/16* (2013.01); *A61M 16/201* (2014.02); *A61M 16/208* (2013.01); *A61M 16/209* (2014.02); *B05B 7/1413* (2013.01); *B05B 7/1486* (2013.01); *F16K 15/144* (2013.01); *F16K 15/147* (2013.01); *F16K 15/185* (2013.01); *G01N 21/53* (2013.01); *A61M 16/0057* (2013.01); *A61M 16/0833* (2014.02); *A61M 16/107* (2014.02); *A61M 16/147* (2014.02); *A61M 2039/242* (2013.01); *A61M 2039/2433* (2013.01); *A61M 2202/0488* (2013.01); *A61M 2202/064* (2013.01); *A61M 2205/3306* (2013.01); *A61M 2205/3334* (2013.01); *B05B 1/32* (2013.01); *B05B 7/1422* (2013.01); *F16K 15/145* (2013.01); *Y10T 137/788* (2015.04); *Y10T 137/7881* (2015.04); *Y10T 137/7882* (2015.04); *Y10T 137/7883* (2015.04); *Y10T 137/7884* (2015.04); *Y10T 137/7885* (2015.04); *Y10T 137/7886* (2015.04)

(58) Field of Classification Search
CPC ............ A61M 16/0833; A61M 16/107; A61M 16/147; A61M 16/16; A61M 16/201; A61M 16/208; A61M 16/209; A61M 2039/242; A61M 2039/2433; A61M 2202/0488; A61M 2202/064; A61M 2205/3306; A61M 2205/3334; A61M 39/24; B05B 1/32; B05B 7/1413; B05B 7/1422; B05B 7/1486; F16K 15/147; F16K 15/185; F16K 15/144; F16K 15/145; G01N 21/53; Y10T 137/788; Y10T 137/7881; Y10T 137/7882; Y10T 137/7883; Y10T 137/7884; Y10T 137/7885; Y10T 137/7886
See application file for complete search history.

(56) References Cited

U.S. PATENT DOCUMENTS

| | | |
|---|---|---|
| 2003/0009079 A1 | 1/2003 | Beaufore et al. |
| 2003/0116197 A1* | 6/2003 | Taylor .................. F16K 15/183 137/522 |
| 2004/0099266 A1 | 5/2004 | Cross et al. |
| 2005/0217668 A1 | 10/2005 | Figley et al. |
| 2007/0215150 A1* | 9/2007 | Boehm ................. A61M 11/06 128/203.12 |
| 2008/0041393 A1 | 2/2008 | Bracken |
| 2009/0000615 A1* | 1/2009 | Pohlmann .............. A61M 11/06 128/200.21 |
| 2010/0199982 A1 | 8/2010 | Hansen |
| 2014/0261420 A1* | 9/2014 | Dwyer ................ A61M 16/164 128/204.14 |

FOREIGN PATENT DOCUMENTS

| | | |
|---|---|---|
| CN | 103002938 A | 3/2013 |
| DE | 4105190 | 8/1992 |
| EP | 0877602 | 11/1998 |
| EP | 1082973 | 3/2001 |
| EP | 1201258 | 5/2002 |
| GB | 2233070 | 1/1991 |
| GB | 2310816 | 9/1997 |
| JP | 2012-524571 A | 10/2012 |
| NL | 6617055 | 4/1968 |
| RU | 2449817 C2 | 5/2012 |
| WO | 92/06703 | 4/1992 |
| WO | 2006/108558 A1 | 10/2006 |
| WO | 2006/136426 | 12/2006 |
| WO | 2007/059083 | 5/2007 |
| WO | 2010/076683 | 7/2010 |
| WO | 2010/122103 A1 | 10/2010 |
| WO | 2012/025496 | 3/2012 |

OTHER PUBLICATIONS

International Search Report and Written Opinion, dated Jun. 1, 2015, International Patent Application No. PCT/EP2015/054244 (21 pages).
Office Action, Russian Patent Application No. 2016134233, dated Jan. 11, 2019 (3 pages).
English translation of NL6617055A, published Apr. 6, 1968, attached to Intention to Grant European Patent Application No. 15706837.0, dated Jul. 19, 2019 (6 pages).

* cited by examiner

DEVICE FOR PROVIDING A CONSTANT AMOUNT OF AEROSOL

TECHNICAL FIELD

The present invention relates to a device for providing an aerosol from an aerosolizable material and to a control system controlling a duckbill valve.

BACKGROUND

Devices for aerosolization ("dry nebulization") of aerosolizable dry material are known in which a reservoir is provided comprising aerosolizable material. The aerosolizable material is fed from the reservoir to an aerosolization channel where the aerosolizable material is mixed with carrier gas which is transmitted through the aerosolization channel in pressure pulses. The aerosolizable material is converted to a state in the aerosolization channel which is referred to as aerosol. The particles of the material are, in this case, present in a preferably uniform and finely dispersed form across the entire volume of the carrier gas and are then discharged from the aerosolization channel.

Such devices can be used for administration of medical substances to spontaneously breathing patients and to mechanically ventilated patients. For use in spontaneously breathing patients, the devices are generally connected to a suitable patient interface (e.g., a mouthpiece or a breathing mask). In invasive use or on mechanically ventilated patients, these devices feed the aerosolizable medical substance into a ventilator system which then delivers the aerosolized material to the patient. Possible configurations of such a device for providing the aerosol are described in WO 2006/108558 A1 and WO 2010/122103 A1.

The aerosolizable material contains a therapeutically active substance. In many clinical situations it is desirable to introduce this active substance into the airways of a patient. In order to make sure that an as large as possible fraction of the inhaled particles is deposited in the desired section of the airways (usually the alveoles in the deep lung), it is important that the particles have the right size. By way of example, it has been found that particles which should reach the deep lung should have a mass median aerodynamic diameter (MMAD) in the range of 0.05-10 µm, preferably between 1-5 µm or approximately 3 µm.

Depending on the particular formulation of the therapeutically active substance to be aerosolized, different technical solutions have been proposed. Liquid formulations such as solutions or suspensions can be aerosolized using nebulizers such as a jet nebulizer, hydrosonic wave nebulizer, or pressurized metered dose inhaler (MDI). Dry powder formulations can be aerosolized by use of a dry powder inhaler, DPI. One possible field of application is the application of a pulmonary surfactant or lung surfactant to a patient.

In vertebrates, the inner lung surfaces involved in gas exchange are covered by a thin film of a substance mixture called "pulmonary surfactant" or "lung surfactant". The most important components of lung surfactant are phospholipids and the so-called surfactant proteins, SP-A, SP-B, SP-C and SP-D. Lung surfactant has surface active properties and reduces surface tension in the alveoli and small airways to such an extent that collapse of the alveoli during exhalation is avoided. The surface tension is regulated dynamically so that the collapse of the alveoli and small airways in favor of the greater ones, which is to be expected according to Laplace's law, is prevented by appropriate adaptation of the surface tension. On the other hand, reduction of surface tension in the alveolar region increases pulmonary compliance, meaning that it facilitates the expansion of the lung upon breathing. The presence of lung surfactant results in a well-balanced and physiologically stable structure of the lung and is vital for the normal function of this organ. While at the time of birth the lungs of mammals contain a sufficient amount of endogenous lung surfactant in order to ensure unrestrained functionality of the lungs from the first breath on, the lungs of prematurely born babies (born below 32 weeks of gestation and especially born below 29 weeks of gestation) are not or not sufficiently capable of producing lung surfactant. This leads to a life-threatening deficiency of oxygen uptake (Infant Respiratory Distress Syndrome, IRDS). IRDS is the main cause of death in prematurely born babies.

Lung surfactant preparations useful to treat Respiratory Distress Syndrome (RDS) such as IRDS can be obtained from the lungs of animals or can be manufactured using the individual components as starting material. For example, WO 92/06703 describes the production of synthetic lung surfactant preparations by evaporating chloroform from a solution comprising phospholipids (such as dipalmitoyl-phosphatidylcholine (DPPC) and dioleylphosphatidyl-ethanolamine (DOPE)) and cholesterol using a rotary evaporator to obtain a thin film which is resuspended in a buffer, if desired together with suitable proteins. EP 0 877 602 discloses the preparation of a synthetic lung surfactant by spray drying a solution of DPPC, palmitoyloleoylphosphatidyl-glycerol (POPG), palmitic acid, calcium chloride and surfactant protein SP-C.

In certain systems known from the art the aerosolizable material is fed to an aerosolization channel by pressure pulses applied to the aerosolization channel. Examples for such devices are described in WO 2006/108558 A1 and WO 2010/122103 A1. In such a device there is normally an open connection between the reservoir comprising the aerosolizable material and the aerosolization channel. The pressure differences occurring when a patient is inhaling or exhaling or which occur at ventilated patients are also transferred to the reservoir comprising the aerosolizable material. Pressure changes also may occur in case of ventilated patients when the tubing used to provide the patient with breathing air is partly or totally blocked, or if one of the tubes of the ventilation system snaps off. When a blockage occurs, the pressure in the reservoir may also rise. As the amount of aerosolizable material provided to the aerosolization channel mainly depends on the pressure difference between the reservoir and the aerosolization channel, an increased pressure in the reservoir may lead to a larger amount of aerosolizable material provided to the aerosolization channel, which then can be too large to be uniformly dispersed in the compressed gas.

SUMMARY

Accordingly, a need exists to provide a device providing an aerosol which provides a substantially constant amount of aerosolized material during use and which provides an aerosol characterized by a substantially constant density of aerosolized material. While, in a preferred embodiment, the aerosolizable material is a powder, it would be conceivable to use the present invention in the aerosolization of a liquid (e.g., a solution or an emulsion).

This need is met by the present invention having the features of the independent claims. Further embodiments are described in the dependent claims.

According to a first aspect, a device for providing an aerosol from an aerosolizable material is provided, the device comprising an aerosolization channel preferably located within an aerosolization unit through which pressure pulses of a carrier gas are passed. Furthermore, a reservoir is provided comprising the aerosolizable material from where the material is provided to the aerosolization channel in which the aerosolizable material is entrained in the carrier gas. WO 2006/108558 does disclose such a device, wherein pulses of pressurized gas are traveling through a capillary, the end of which is positioned in the aerosolization channel, in an area below an opening of the reservoir towards the aerosolization channel. This configuration results in a Venturi effect, such that aerosolizable material is sucked out of the reservoir into the aerosolization channel, where it is entrained in the flow of gas. In addition to these features, the device according to the invention comprises a material providing valve located between the reservoir and the aerosolization channel which opens in the direction of the aerosolization channel and which is configured to be opened or closed by a pressure difference between the reservoir and the aerosolization channel. The material providing valve, in an open state, provides the aerosolizable material to the aerosolization channel. The material providing valve helps to keep the pressure in the reservoir substantially constant and especially helps to prevent excess pressure (or positive pressure), if it occurs in the aerosolization channel, from being propagated to the reservoir. As a consequence, a situation can be avoided where an excess pressure in the reservoir causes an unwanted increase of the amount of aerosolized material in the generated aerosol as soon as the pressure in the reservoir exceeds the pressure in the aerosolization channel.

Preferably, the material providing valve is configured in such a way that it is closed when no pressure difference between the reservoir and the aerosolization channel exists, and is open when the pressure difference between the reservoir and the aerosolization channel is larger than a predefined positive value. In other words, when the pressure in the aerosolization channel is lower than in the reservoir (as usually is the case during the pressure pulses mentioned above, due to the induced Venturi effect), the material providing valve will be in an open state. It should be understood that there is not one single open state. Rather, the opening degree of the material providing valve (or, in other words, the cross-sectional area of the valve's opening) can vary, especially in dependence on the pressure difference between the reservoir and the aerosolization channel. Normally, the larger the pressure difference between the reservoir and the aerosolization channel is, the larger the opening degree of the material providing valve will be (the wider open the valve will be). In one embodiment, the material providing valve is a duckbill valve (also known as duckbill check valve). This type of valve has been found to be particularly suitable for providing the aerosolizable material to the aerosolization channel. Among others, this type of valve has the advantage that the aerosolizable material passes through the valve following a substantially linear path, thus preventing or minimizing any clogging of the valve by a compaction of aerosolizable material. It should be understood that any other valve may be used which can provide a powdered dry material or a liquid to the aerosolization channel. The duckbill valve can be made of a flexible synthetic, e.g. silicone, rubber or any other flexible material. The amount of aerosolizable material provided by the duckbill valve in response to a given pressure difference between reservoir and aerosolization channel can be set by selecting the length of the duckbill, the used material, especially the material's elasticity, and/or the geometry of the duckbill.

It is possible that the device furthermore comprises a control module for controlling the material providing valve which is configured to control the amount of aerosolizable material provided to the aerosolization channel. In one embodiment the control module comprises a force applying element capable of applying a mechanical force to the material providing valve. The force applying element, via the applied mechanical force, can influence the amount of aerosolizable material provided to the aerosolization channel by controlling an opening degree of the material providing valve (i.e., controlling the cross-sectional area of the valve's opening). The force applying element may apply a preload to the material providing valve in order to influence an opening degree when a pressure difference between the reservoir and the aerosolization channel exists. The force applying element may have the form of a wedge which can apply a force to a longitudinal side surface of the duckbill valve.

The control module may furthermore comprise a force translating unit which translates the generated mechanical force to the force applying element which then applies the mechanical force to the material providing valve.

The control module can furthermore comprise an actuating element which is configured to generate and control the mechanical force applied to the material providing valve. The actuating element can be used to control the amount of the applied force and, as will be explained later, can also control the direction of the applied force. The actuating element can apply the generated mechanical force to the force translating unit which transmits the generated mechanical force to the force applying element.

The force applying element can be connected to the duckbill valve in such a way that it is configured to apply a pulling force on the duckbill valve to actively open the duckbill valve. The force applying element can further apply a compression force in a direction opposite to the pulling force by which a preload is applied to the duckbill valve which controls the opening degree of the duckbill valve when the duckbill valve is opened by the pressure pulse. A compression force is applied by the force applying element when the latter is pressed against a side surface of the duckbill valve. When a fixed connection between the force applying element and the duckbill valve is provided, also a pulling force can be applied to the duckbill valve to actively open the duckbill valve. This pulling force may be necessary to open the duckbill valve independently of the generated pressure pulses. By way of example, during use it may happen that aerosolizable material is stuck in the lips of the duckbill valve, or that aerosolizable material forms a clot clogging the valve. In such a situation the valve can be actively opened by actuating the actuating element and by generating a pulling force which pulls the duckbill valve open. To this end the force applying element can be fixedly connected to the duckbill valve, and the actuating element can be fixedly connected to the force applying element. Then, the next pressure pulse or pulses will purge any material stuck in or clogging the duckbill valve out of the valve. In one embodiment, the force translating unit and the force applying element may be provided as a one-piece element. In this embodiment it is enough to fixedly connect the actuating element to the force translating unit. By way of example, the actuating element may be a screw or a similar element connected to the force translating unit or the force applying element. The screw may be provided in a threaded part of the control module, and by turning the screw in one or the other direction either a pulling force or a compression force can be applied to the duckbill valve.

The reservoir may furthermore comprise an air inlet valve which opens in the direction of the reservoir and is configured to keep a predefined air pressure in the reservoir. If the reservoir was airtight with respect to the ambient air, upon feeding aerosolizable material to the aerosolization channel a negative pressure would be generated in the reservoir, causing less or no aerosolizable material to be provided to the aerosolization channel. Towards this end, an air inlet valve is provided which helps to maintain the reservoir at a predefined air pressure.

In another embodiment the reservoir can comprise a pressure compensation valve which connects the reservoir to the auxiliary air channel and which is actuated when the material providing valve remains stuck in an open state. Such pressure compensation valve opens in the direction of the auxiliary air channel when a pressure in the reservoir is higher than a pressure in the aerosolization unit. When the material providing valve remains stuck in an open state, an excess pressure may be generated in the reservoir, e.g. by the ventilator air provided to the patient or by the breathing patient. In such a situation, the pressure compensation valve will allow to depressurize the reservoir. This pressure compensation valve is connected via a suitable tubing or channel with a part of the auxiliary air channel where the pressure pulses to generate the aerosol are not present anymore, or at least have been dampened to an acceptable level.

This pressure compensating valve may be configured to open at a pressure difference that is approximately ten to twenty times lower than the pressure difference needed to open the material providing valve. By way of example, the pressure difference needed to open the material providing valve may be higher than 100 mbar, whereas the pressure compensating valve may already open at a pressure difference of approximately 5 mbar.

The device may furthermore contain a sensing element configured to determine the amount of aerosolized material in the generated aerosol. This sensing element can be used in a feedback control circuit. By way of example, the sensing element may be configured to control the force applying element in dependence on a deviation of the determined amount of aerosolized material in the generated aerosol from a predefined amount of aerosolized material in the generated aerosol. If the sensing device determines that the generated aerosol contains too little aerosolized material, the force applying element may be controlled in such a way that less preload is applied to the material providing valve so that a larger opening degree of the valve is obtained. If, on the other hand, it is determined that the amount of aerosolized material in the generated aerosol is too high, the preload generated by the force applying element may be increased in order to decrease the opening degree of the valve and in order to decrease the amount of aerosolizable material provided by the valve in response to a pressure pulse.

The invention furthermore relates to a control system comprising a duckbill valve configured to supply a fluid in a flow direction and to prevent a flow of the fluid in the direction opposite to the desired flow direction. The term "fluid" as used here is to be understood in the usual way (a substance that shows flowing behaviour when a shearing force is applied) and particularly refers to powdered solid substances (e.g., a medicinal dry powder formulation) and to liquids (e.g., solutions and suspensions). The control system furthermore comprises a control module configured to control the amount of fluid supplied by the duckbill valve in the flow direction in an open state of the duckbill valve. The control module comprises a force applying element configured to apply a mechanical force onto the duckbill valve, and the force applying element, via the applied mechanical force, is configured to influence the amount of fluid provided by the duckbill valve in the open state. The control module may be configured as discussed above in more detail in connection with the device. The fluid can be an aerosolizable material. The fluid can be provided in the form of a dry powder or may be a liquid. The fluid may contain a therapeutically active substance such as a lung surfactant or any other therapeutically active substance.

The invention will be described in further detail below with reference to the accompanying drawings.

DETAILED DESCRIPTION

Figure 1:
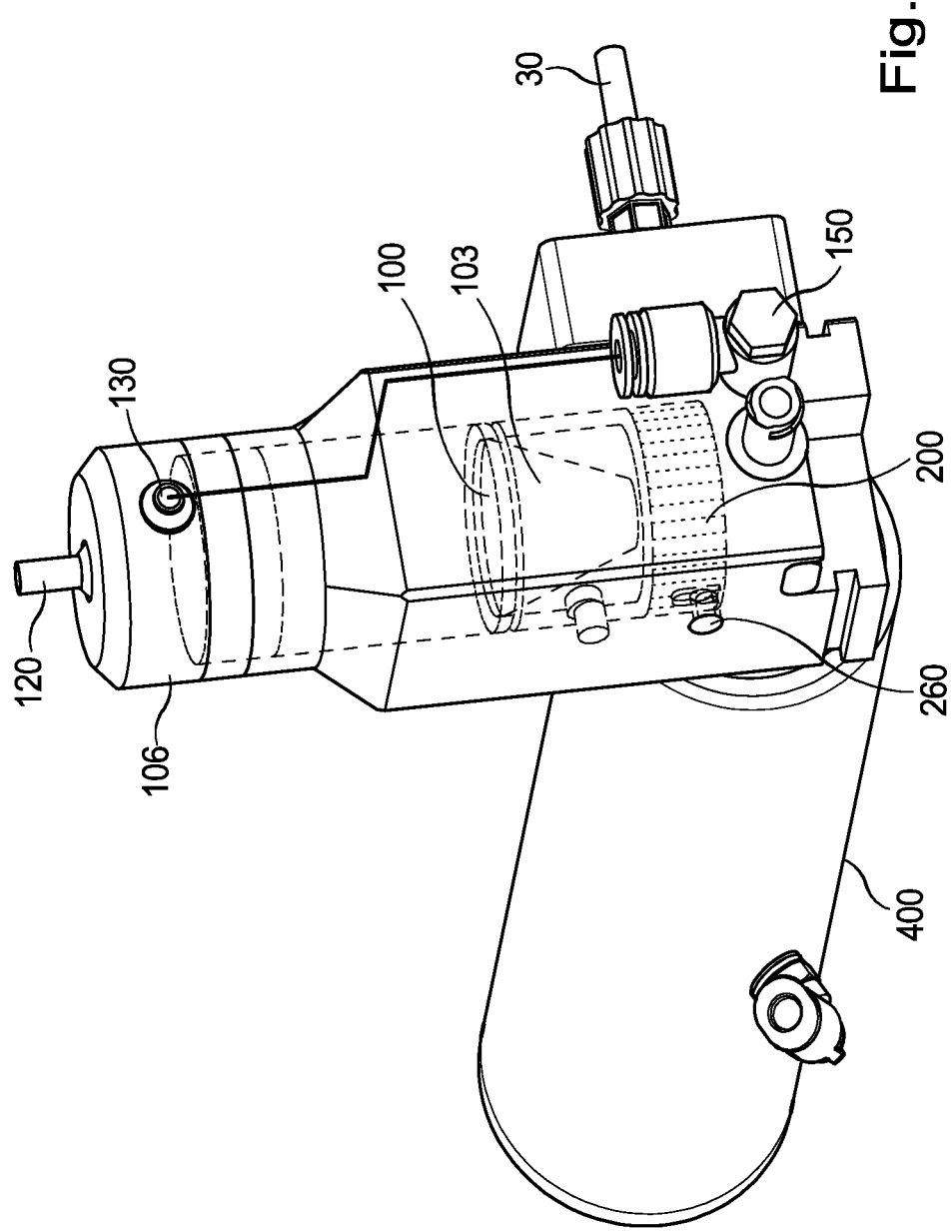
FIG. 1 shows a schematic side elevation view of a device for providing an aerosol including a material providing valve.

In connection with FIGS. 1 and 2, the device for providing an aerosol will be described in further detail, wherein in FIGS. 3 and 4 a control mechanism configured to control the amount of aerosolizable material provided to an aerosolization channel of the device will be explained in more detail.

The device for providing an aerosol comprises a reservoir 100 for the aerosolizable material, i.e. powdery material to be aerosolized. The reservoir 100 comprises an outer wall 101 and an inner cylindrical wall 102. The reservoir furthermore comprises a funnel-like tapered wall 103. Some or all of the walls 102, 103 can be self-exciting membranes made of e.g. medical grade silicone preferably having a wall thickness of about 0.5 mm. Where a wall is formed by a self-exciting membrane, there are spaces formed between the outer wall 101 and the cylindrical and conical walls 102 and 103. Regarding any details of the use of self-exciting membranes as inner walls of an aerosolization device, reference is made to WO 2010/122103 A1. At the bottom of the reservoir, an aperture 105 is located above an aerosolization unit 300 which comprises a capillary tube 350, a chamber, an aerosolization channel 360 and a dispersing nozzle 370. The aerosolization unit 300 is configured such that the capillary tube 350 is, via the chamber and the aerosolization channel 360, in fluid flow connection with the dispersing nozzle 370. In addition, the aerosolization unit 300 is configured such that, when the unit is in its operating position under the reservoir within the device for providing an aerosol and provided the material providing valve 210 is in an open state, the capillary tube 350 is, via the chamber and the aperture 105, in fluid flow connection with the reservoir 100. On top of the reservoir 100, a lid 106 is provided that tightly closes the reservoir. An air inlet valve 120 is provided which opens in the direction of the reservoir and which is configured to maintain an ambient air pressure in the reservoir. When aerosolizable material is provided through the aperture 105 to the aerosolization unit 300, the air inlet valve 120 provides the amount of air that is needed to keep the pressure inside the reservoir substantially unchanged.

Furthermore, a pressure compensation valve 130 is provided which connects the reservoir with the auxiliary air channel 30. The functioning of this pressure compensation valve will be explained in further detail below with reference to FIG. 5, where the pneumatic situation of the whole device is explained in more detail.

Figure 2:
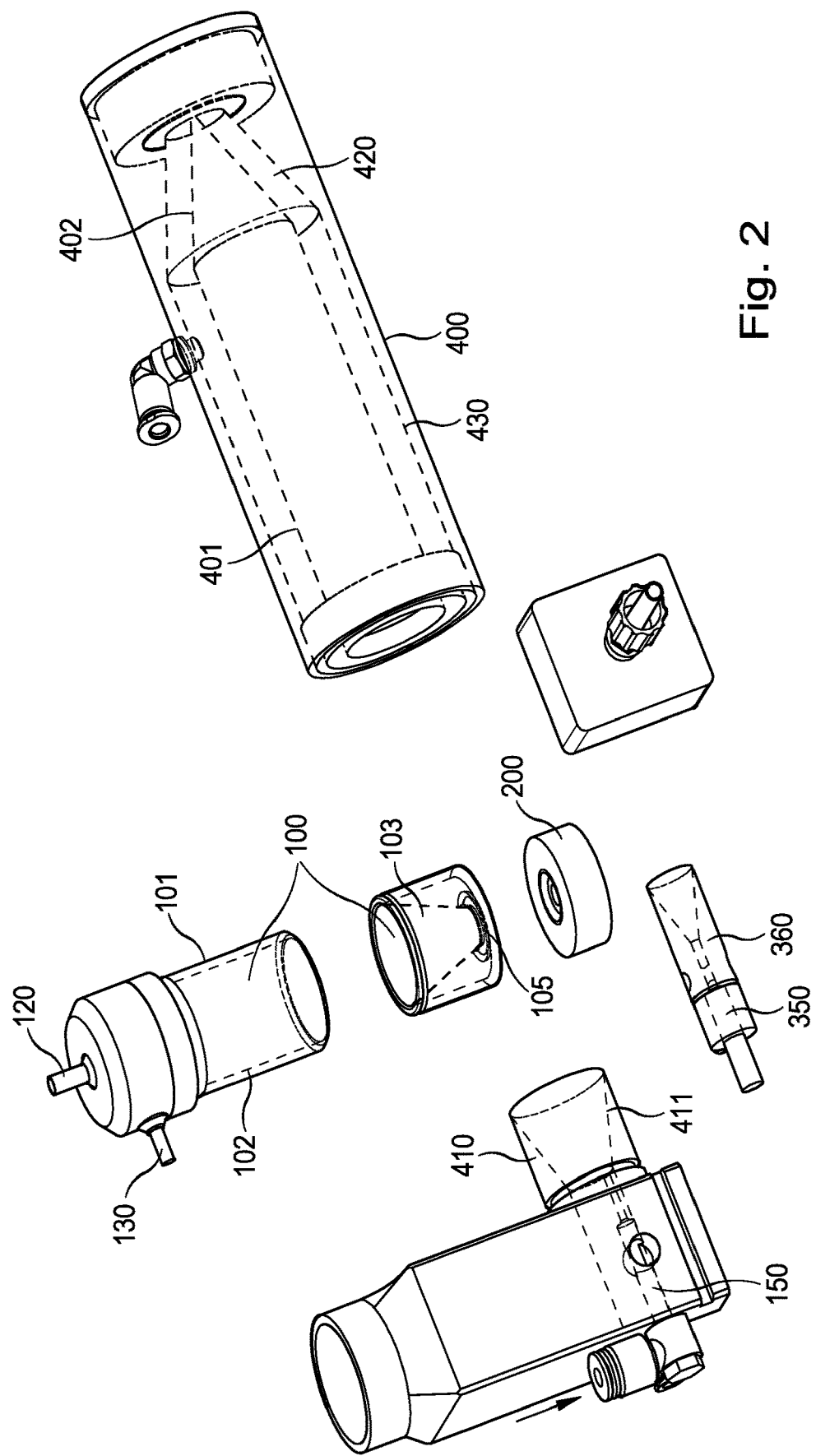
FIG. 2 shows an exploded view of the different components of the device of FIG. 1.

Referring to the embodiment of FIGS. 1 and 2, compressed carrier gas is fed in form of pulses to a capillary tube 350, the end of which protrudes into a chamber. On the opposite side the chamber opens out into an aerosolization channel 360, which in turn opens out into a dispersing nozzle 370 whose cross-section increases continuously in a direction extending away from the capillary tube 350. In operation, pressure pulses of the carrier gas enter the aerosolization channel 360 of the device through the capillary tube 350 and, due to the pressure difference created according to Venturi's principle between the gas exciting the capillary and the reservoir, aerosolizable material is sucked from the reservoir into the aerosolization channel 360, dispersed and entrained in the carrier gas. At the same time, this pressure pulse also acts on tapered membrane wall 103 at the bottom of reservoir 100 and on the membrane walls 401 and 402 of a spacer 400, causing them to bulge and oscillate according to the frequency of the pressure pulses. Thus, aerosolizable material adhering to the walls (if any) is loosened and free to be entrained by the carrier gas stream again. The dispersing nozzle 370 opens into the spacer which comprises a distal portion 410 with conical inner wall 411 and a proximal portion 420 with the conical inner wall 402 tapered proximally, the distal portion 410 and the proximal portion 420 being connected by a central portion 430 with cylindrical inner wall 401. Like the walls of the reservoir, the walls of the spacer can be self-exciting membranes made of, e.g., silicone. Further details of the device shown in FIGS. 1 and 2 can also be taken from WO 2010/122103 A1.

Figure 3:
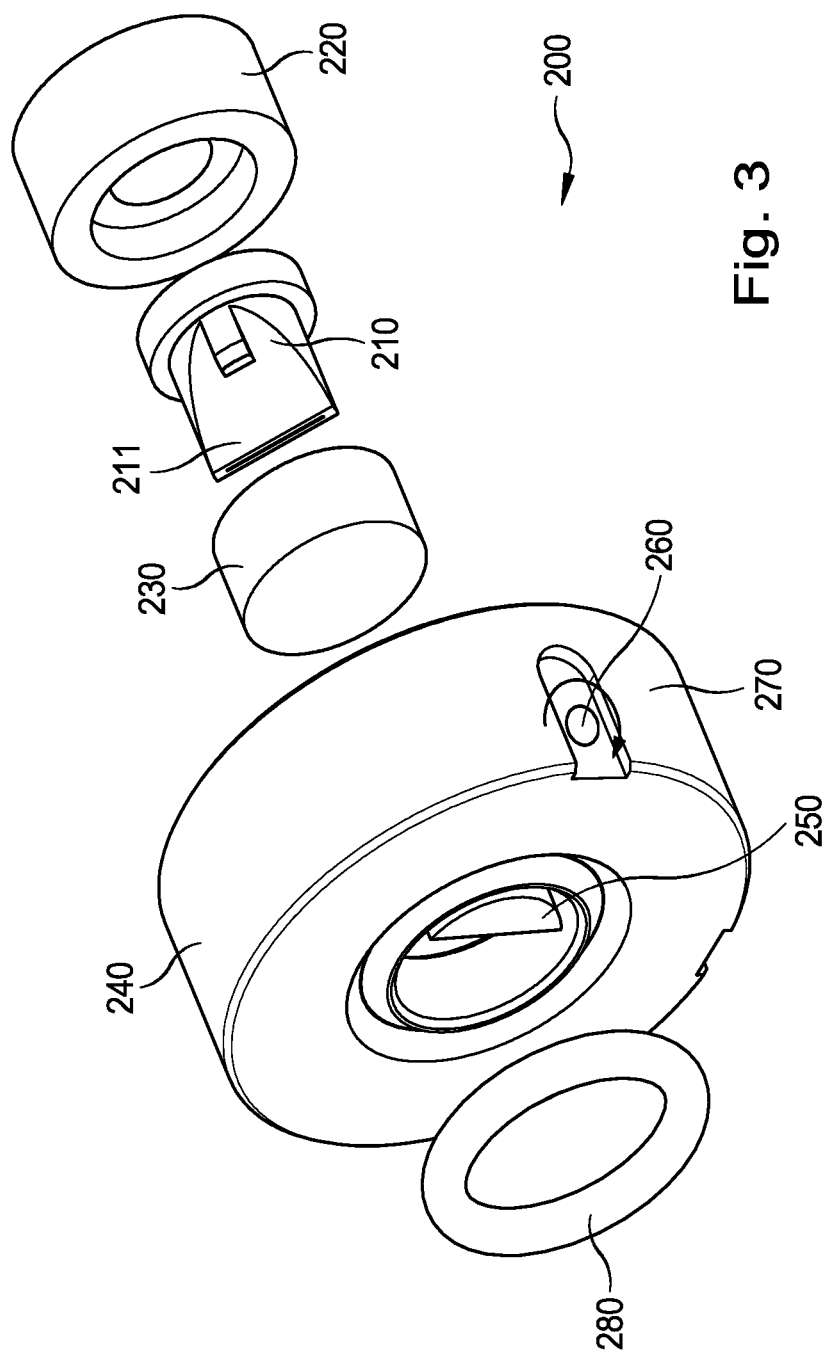
FIG. 3 shows an exploded view of a control module with which the amount of aerosolizable material provided by the material providing device can be controlled.
Figure 4:
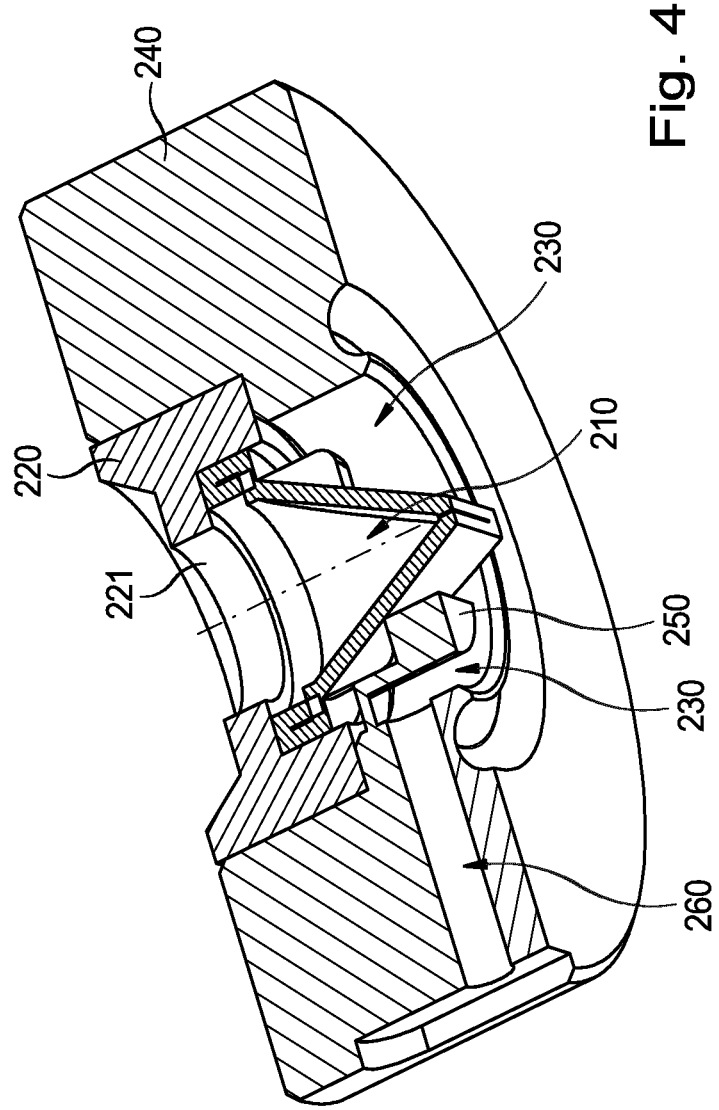
FIG. 4 is a sectional view of the control module of FIG. 3 in an assembled state.

However, other than the device as disclosed in WO 2010/122103 A1, the device according to the invention in addition contains a material providing valve 210 which is shown in FIG. 3 and which is incorporated in a control module 200. The material providing valve 210 opens towards the aerosolization channel 360 and is mainly activated by a pressure difference between the pressure in the reservoir and the pressure in the aerosolization channel 360. When in accordance with Venturi's principle a pressure pulse is generated in the aerosolization channel 360, the pressure in the aerosolization channel will be lower than the pressure in the reservoir and the material providing valve 210 will be opened by this pressure difference.

In the embodiment of FIG. 3 the material providing valve is a duckbill valve (sometimes called a duckbill check valve). This duckbill valve allows a fluid to flow in one direction through a conduit, while closing and preventing back or reverse flow when the direction of the pressure gradient across the valve is reversed. The valve 210 provides an amount of aerosolizable material to the aerosolization channel 360. The amount of aerosolizable material provided by the duckbill valve can be controlled. To this end the control module 200 is provided which will be explained below with reference to FIGS. 3 and 4. The control module comprises a force applying element 250. As shown in FIG. 4, this force applying element can apply a mechanical force to the broad lateral side of the duckbill valve, having the effect of a preload. The preload applied to the duckbill valve can be controlled via an actuating element 260. The actuating element is connected to the force applying element 250, either directly or via a force translating unit 230. The force translating unit 230, which may be a component made of an elastomer, can be placed between the actuating element 260 and the force applying element 250. The force applied to the lateral side surface of the duckbill valve controls the opening degree of the duckbill valve when a pressure pulse in the aerosolization channel 360 occurs. The more preload the force applying element applies to the side surface of the duckbill valve, the smaller the opening degree of the duckbill valve will be. The control module 200 is provided in a housing 240 with a cylindrical side surface 270. The duckbill valve 210 is located on a seat 220 which comprises an opening 221 through which the aerosolizable material from the reservoir will be fed to the duckbill valve 210. A seal ring 280 will help to provide an airtight connection of the control module to the aerosolization channel 360. If desired, a unit formed of valve 210, seat 220, housing 240 and seal ring 280 can be manufactured in one piece, which optionally can also comprise force applying element 250.

The force applying element can not only apply a preload and thus a compression force onto the side surface 211 of the duckbill valve, but also a pulling force can be generated. To this end, the force applying element 250 can be fixedly connected (i.e., attached) to the duckbill valve 210. The actuating element which is also fixedly connected to the force applying element can now pull the valve's side surface 211 in such a way that the control module actively opens the duckbill valve. In normal use, the duckbill valve will be opened by the pressure difference generated by the pressure pulses. However, when aerosolizable material is stuck in the duckbill valve and when the opening of the duckbill valve is clogged with aerosolizable material, it may be necessary to actively open the valve to remove any particle agglomerations which are stuck in the duckbill valve and which impede the proper functioning of the valve.

In one embodiment, the force translating element 230 and the force applying element 250 may be made as a one-piece element, so that the actuating element 260 only needs to be fixedly connected to this one-piece element in order to be able to generate a pulling force which opens the valve.

The amount of aerosolizable material provided by the valve 210 can also be controlled by a proper selection of the material of the duckbill valve and by the selection of the duckbill's geometry and width. The actuating element may be a screw provided in a threaded opening in the control module. This screw may be actuated by a user or by a motor such as a linear motor.

Figure 6:
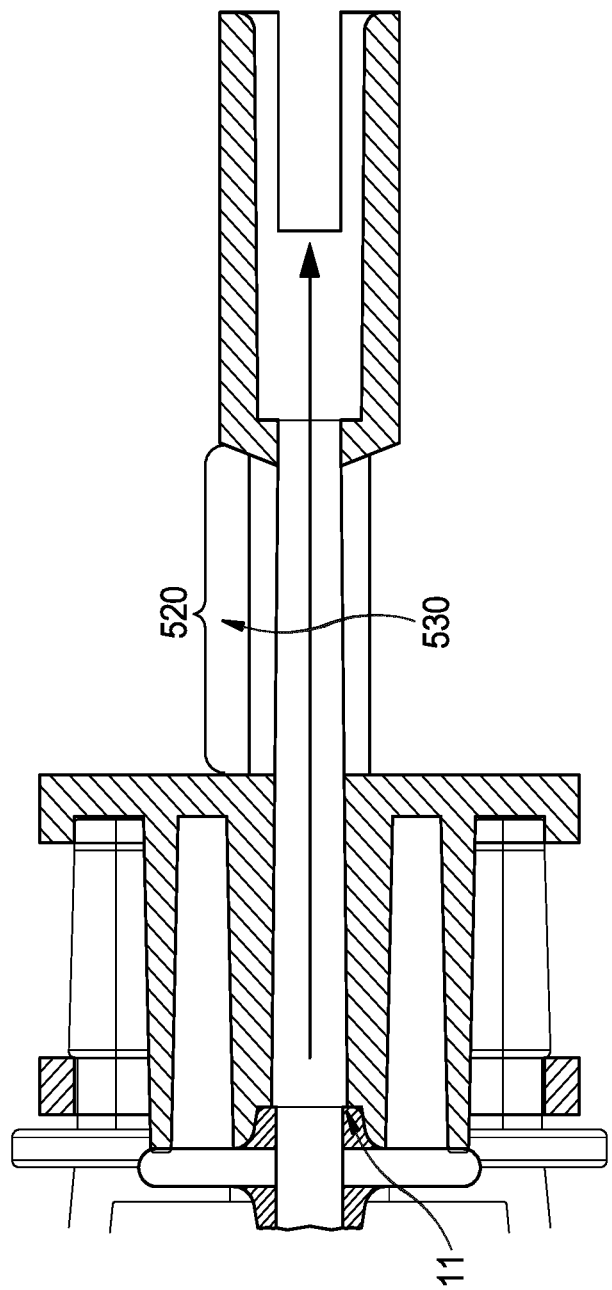
FIG. 6 is a schematic view of a sensing element configured to determine the amount of aerosolizable material in the generated aerosol.
Figure 7:
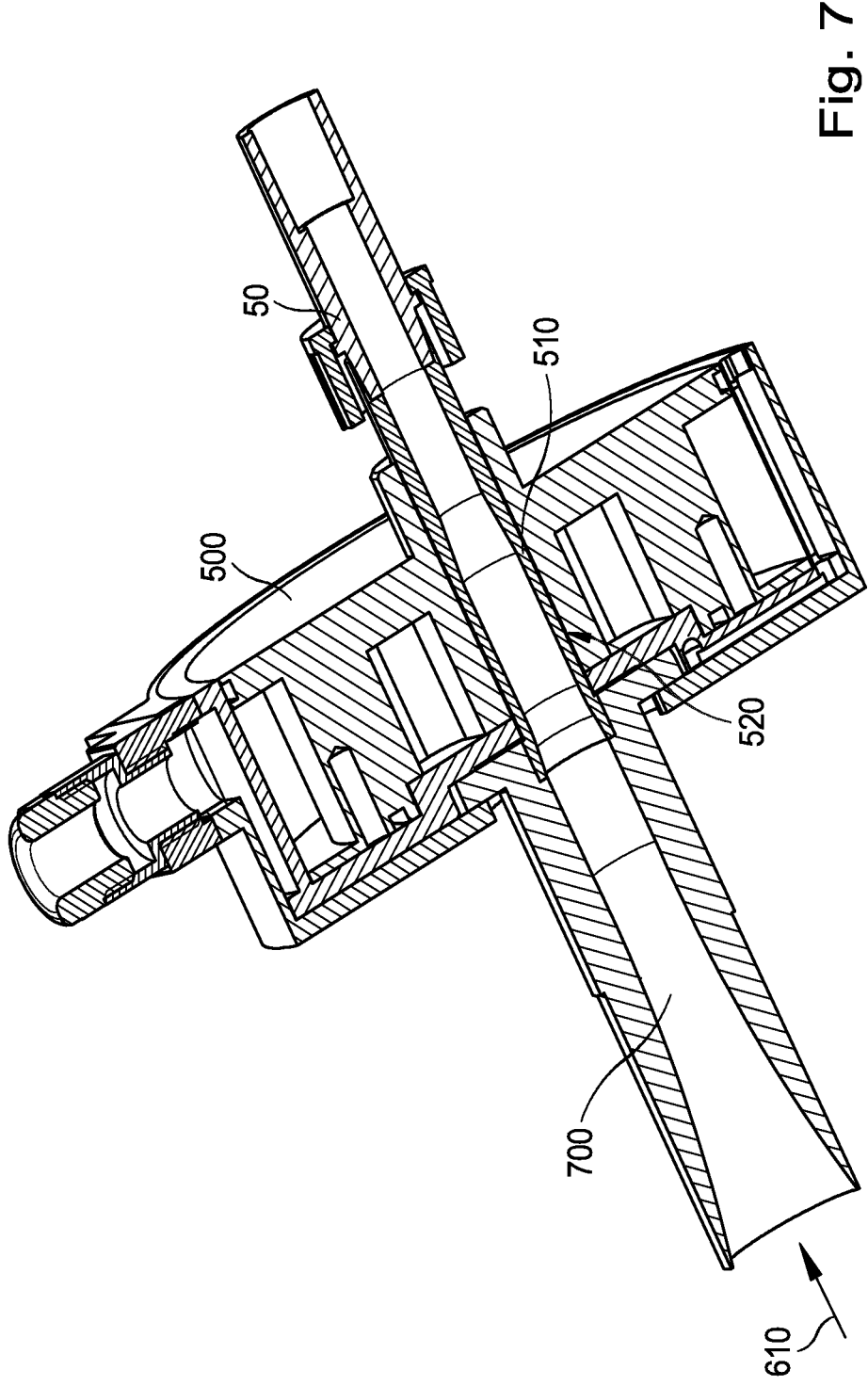
FIG. 7 shows a schematic view of how the sensing element is incorporated into a device for aerosolization.
Figure 8:
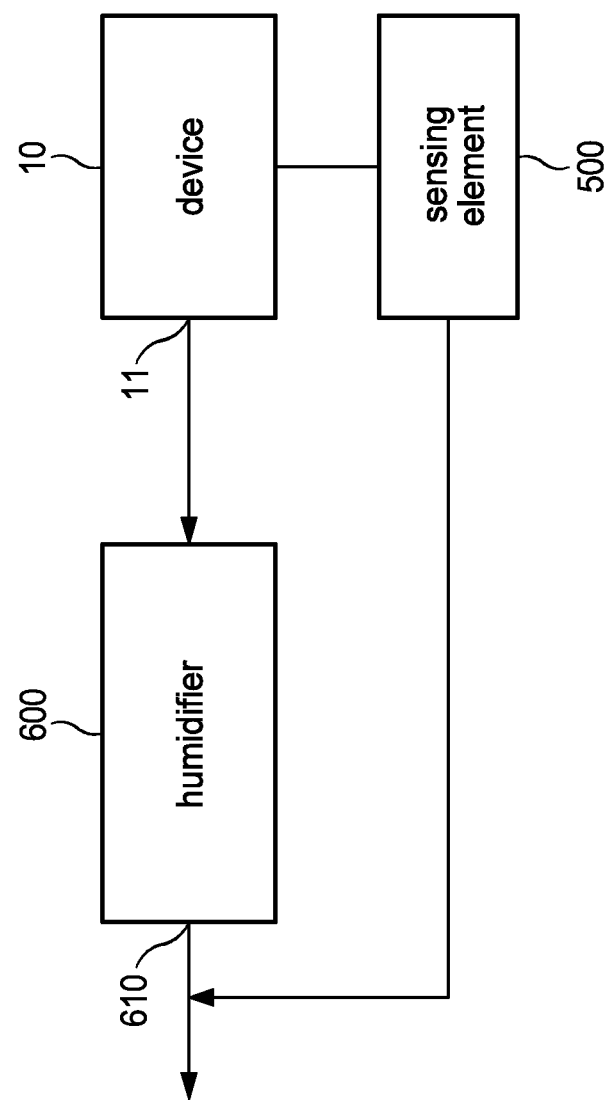
FIG. 8 is a schematic view of how a feedback control circuit is generated with the sensing element to control the amount of aerosolizable material in the generated aerosol.

In connection with FIGS. 6-8, an embodiment is disclosed in which the actuating element will be controlled by a sensing element 500 which is configured to determine the amount of aerosolized material in the generated aerosol. The determination of the amount of aerosolized material in the generated aerosol can be accomplished, e.g., by determining a scattering of a light by the aerosol. The aerosol exiting the device disclosed in connection with FIGS. 1 and 2 will be fed to the sensing element 500. The sensing element can comprise a light source and a detector for the scattered light. The sensing element may be a sensing element as described in DE 4 105 190 A1. The sensing element provided in a housing 510 has a light source 530 as indicated by the arrow in FIG. 6 and the light is fed through a transparent window 520. The particle concentration in the aerosol might be further determined by reduction of the light transmitted from light source 530 through the generated aerosol. It should be understood that any adherence of aerosolized particles to window 520 should be avoided. This might be achieved by using an appropriate form and material of the inner surface of the transparent window 520.

In the embodiment shown in FIG. 7, a connecting element 700 is provided through which the aerosol in the direction of the arrow enters the sensing element 500 and leaves the sensing element via connector 50 to which a tube can be connected further guiding the aerosol. The sensing element will determine the particle concentration in the aerosol. If the particle concentration is within a predefined range or if the particle concentration corresponds to a predefined value, no action is taken. If the determined particle concentration is too low, the sensing element may transmit this information to the control module, e.g. to a linear motor controlling the control element, and the linear motor may then control the actuating element 260 in such a way that the preload applied to the side surface 211 of the duckbill valve 210 is lowered. If the particle concentration in the aerosol is too high, the linear motor may be controlled in such a way that the actuating element transmits a higher force to the force applying element so that the preload onto the valve's side surface is increased. This increased preload will reduce the opening degree of the material providing valve when a pressure pulse arrives in the aerosolization unit 300, thus reducing the amount of aerosolizable material sucked into the aerosolization channel 360 by the pressure pulse.

In the embodiment of FIG. 8, the device for aerosolization is connected to a humidifier 600. As described in WO 2012/025496 A1, the generated aerosol may be humidified before it is administered to a patient. The humidification step helps to prevent the particles in the aerosol from agglomerating. In the embodiment of FIG. 8, the sensing element is provided directly at the exit 610 of the humidifier 600. However, it should be understood that the sensing element may also be provided directly at the exit 11 of the device for aerosolization as shown in FIG. 6, or at any other position of the aerosol's flow path.

Figure 5:
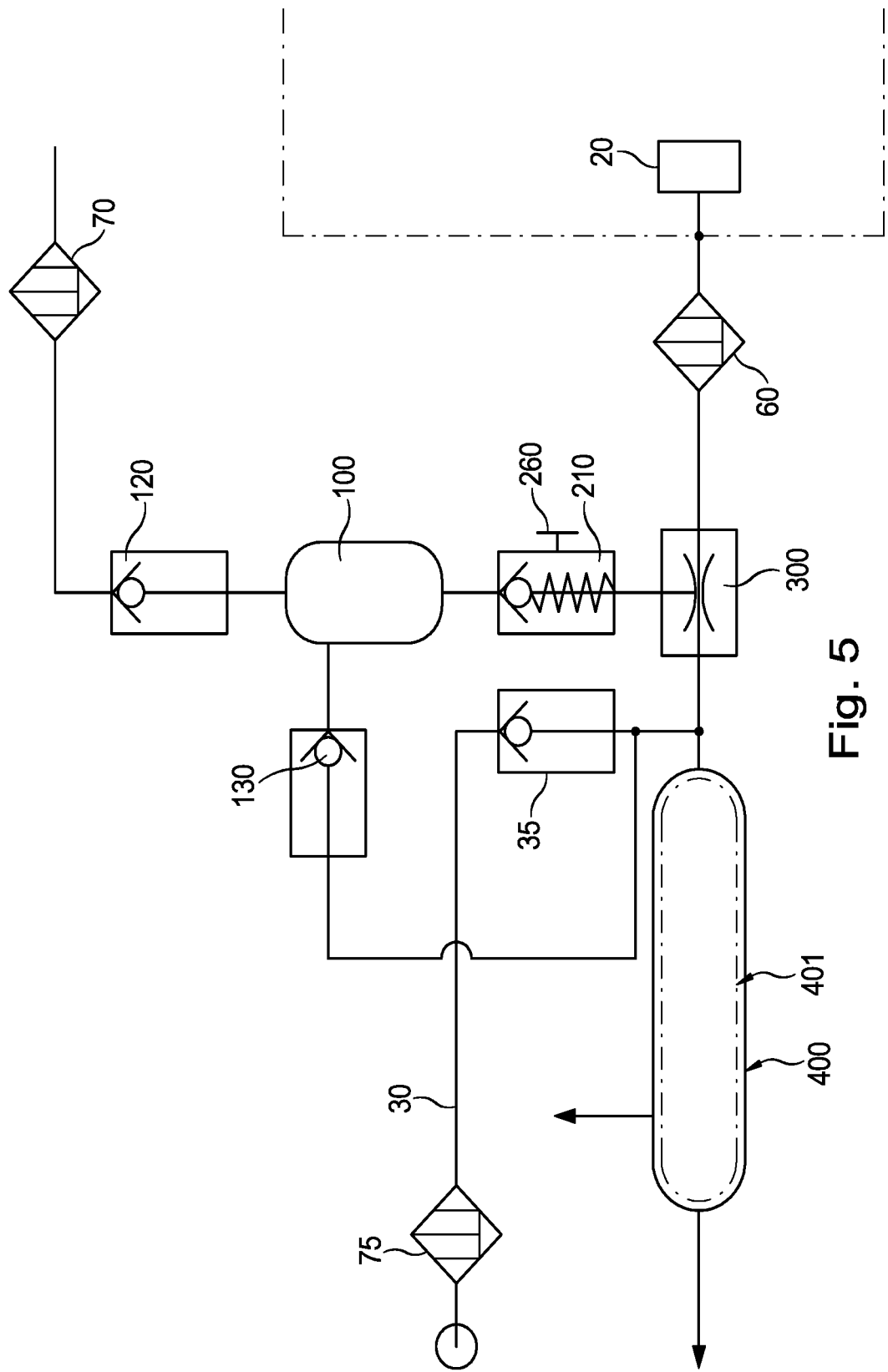
FIG. 5 is a schematic view of the pneumatics in the device of FIG. 1.

In FIG. 5, a pneumatic plan of the device for aerosolization is shown. A source 20 of pressure gas transmits pressure pulses to the aerosolization unit 300 after having passed a filter 60. The reservoir 100 is schematically shown which is connected via an air inlet valve 120 to the ambient air, wherein a filter 70 may be provided before the ambient air enters the reservoir 100. As can be seen from FIG. 5, the air inlet valve opens in the direction of the reservoir. The material providing valve 210 is schematically shown between the reservoir 100 and the aerosolization unit 300. Furthermore, the actuating element 260 is schematically shown via which the amount of fluid provided by the valve can be controlled. The generated aerosol is fed from the aerosolization channel to spacer 400 which contains the inner walls 401.

Between the spacer and the aerosolization unit 300 an auxiliary connecting line 30 supplies unpulsed air to the spacer to thereby flush the spacer of residues of aerosolizable material. A filter 75 is provided to block contamination by undesired particles. A valve 35 is provided between the spacer and the supplied unpulsed air to prevent pressure pulses from propagating in the direction of the supplied air and to assure that the supplied air can be supplied to the device. As shown in FIG. 5, a pressure compensation valve 130 is provided which is connected between the reservoir 100 and the line connecting the aerosolization unit 300 to the spacer 400. This pressure compensation valve only opens in the direction of the spacer or aerosolization unit and can help to remove an undesired higher pressure from the reservoir. When the material providing valve is clogged with aerosolizable material, e.g. when the material agglomerates in the duckbill so that the duckbill cannot be closed anymore, the air supply of the unpulsed air 30 may generate a high pressure in the reservoir. For example, the unpulsed air may be supplied at a rate of 0.7 liter/min. This higher pressure in the reservoir 100 can be avoided with the use of pressure compensation valve 130. This pressure compensation valve may open at a pressure difference between the reservoir and the spacer or aerosolization unit of, e.g., 5 mbar. The pressure compensation valve opens when the pressure in the reservoir is higher than in the spacer or aerosolization unit and feeds the pressure back into the aerosolization channel via a return channel 150 shown in FIGS. 1 and 2. The pressure compensation valve 130 opens at a pressure difference which is much lower than the pressure difference needed to open the material providing valve if it worked properly. By way of example, the pressure difference needed to open the properly functioning material providing valve may be around 100 mbar. The pressure compensation valve transmits the generated pressure in the reservoir back into the system. This pressure compensation valve helps to make sure that the amount of additional aerosolizable material that is fed to the aerosolization unit is minimized.

The invention claimed is:
1. A device for providing an aerosol from an aerosolizable material, the device comprising:
    an aerosolization unit through which pressure pukes of a carrier gas are passed,
    a reservoir comprising the aerosolizable material and which provides the aerosolizable material to the aerosolization unit where the aerosolizable material is entrained by the carrier gas,
    a duckbill valve located between the reservoir and the aerosolization unit which opens towards the aerosolization unit and which is configured to be opened and closed by a pressure difference between the reservoir and the aerosolization unit and which provides, in an open state, the aerosolizable material to the aerosolization unit, wherein the aerosol is output from the aerosolization unit;
    a force applying element fixedly connected to the duckbill valve to provide a mechanical force to a side surface of the duckbill valve;
    an actuating element fixedly connected to the force applying element, wherein the force applying element and the actuating element are configured to cooperate together to apply a pulling force to the duckbill valve to actively open the duckbill valve and to apply a compression force in a direction opposite to the pulling force by which a preload can be applied to the duckbill valve which controls the opening degree of the duckbill valve when the duckbill valve is opened by a pressure pulse.
2. The device according to claim 1, wherein the duckbill valve is configured in such a way that it is closed when no pressure difference between the reservoir and the aerosolization unit exists and is open when the pressure difference between the reservoir and the aerosolization unit is larger than a predefined positive value.

3. The device according to claim 1, wherein the actuating element is fixedly connected to the force applying element by a force translating unit.

4. The device according to claim 1, wherein the reservoir comprises an air inlet valve which opens in the direction of the reservoir and which is configured to keep an ambient air pressure in the reservoir.

5. The device according to claim 1, wherein the reservoir comprises a pressure compensation valve.

6. The device according to claim 5, wherein the pressure compensation valve is configured to open at a pressure difference that is 10 to 20 times lower than the pressure difference needed to open the duckbill valve.

7. The device according to claim 1, further comprising a sensing element configured to determine the amount of aerosolizable material in the aerosol.

8. The device according to claim 7, wherein the sensing element is configured to control the force applying element in dependence of a deviation of the determined amount of aerosolizable material in the aerosol from a predefined amount of aerosolizable material in the aerosol.

9. A device for providing an aerosol from an aerosolizable material, the device comprising:
   an aerosolization unit that includes a passageway that is configured to pass pressure pulses of a carrier gas;
   a reservoir connected to the aerosolization unit, the reservoir containing the aerosolizable material, and the reservoir includes an output that is in communication with the passageway of the aerosolization unit to provide the aerosolizable material to the aerosolization unit so that the aerosolizable material is entrained by the carrier gas;
   a duckbill valve that controls the passage of the aerosolizable material through the output, the duckbill valve opens towards the aerosolization unit and the duckbill valve is configured to be opened and closed by a pressure difference between the reservoir and the aerosolization unit, wherein the aerosol is output from the aerosolization unit;
   a force applicator fixedly connected to the duckbill valve to provide a mechanical force to a side surface of the duckbill valve;
   an actuator fixedly connected to the force applicator to actuate the force applicator in a pulling direction and in a compression direction, wherein the force applicator applies a pulling force to the side surface of the duckbill valve to actively open the duckbill valve when the actuator actuates the force applicator in the pulling direction, and the force applicator applies a compression force to the side surface of the duckbill valve when the actuator actuates the force applicator in the compression direction.

10. The device according to claim 9, wherein the duckbill valve is closed when no pressure difference between the reservoir and the aerosolization unit exists and the duckbill valve is open when the pressure difference between the reservoir and the aerosolization unit is larger than a predefined positive value.

11. The device according to claim 9, wherein the actuator is fixedly connected to the force applicator by a force translating unit.

12. The device according to claim 9, wherein the reservoir comprises an air inlet valve which opens in the direction of the reservoir and which is configured to keep an ambient air pressure in the reservoir.

13. The device according to claim 9, wherein the reservoir comprises a pressure compensation valve.

14. The device according to claim 13, wherein the pressure compensation valve is configured to open at a pressure difference that is 10 to 20 times lower than the pressure difference needed to open the duckbill valve.

15. The device according to claim 9, further comprising a sensor mounted to the aerosolization unit that determines the amount of aerosolizable material in the aerosol.

16. The device according to claim 15, wherein the sensor is electrically connected to the actuator so that an output signal of the sensor controls the actuator.

* * * * *